US012700506B2

(12) United States Patent
Sadeghi-Naini et al.

(10) Patent No.: US 12,700,506 B2
(45) Date of Patent: Aug. 4, 2026

(54) DEEP LEARNING OF QUANTITATIVE ULTRASOUND MULTI-PARAMETRIC IMAGES AT PRE-TREATMENT TO PREDICT BREAST CANCER RESPONSE TO CHEMOTHERAPY

(71) Applicants: Sunnybrook Research Institute, Toronto (CA); Ali Sadeghi-Naini, Maple (CA); Hamidreza Taleghamar, Toronto (CA)

(72) Inventors: Ali Sadeghi-Naini, Maple (CA); Hamidreza Taleghamar, Toronto (CA); Gregory J. Czarnota, Toronto (CA)

(73) Assignee: Sunnybrook Research Institute, Toronto (CA)

( * ) Notice: Subject to any disclaimer, the term of this patent is extended or adjusted under 35 U.S.C. 154(b) by 218 days.

(21) Appl. No.: 18/832,320

(22) PCT Filed: Jan. 23, 2023

(86) PCT No.: PCT/CA2023/050074
§ 371 (c)(1),
(2) Date: Jul. 23, 2024

(87) PCT Pub. No.: WO2023/137563
PCT Pub. Date: Jul. 27, 2023

(65) Prior Publication Data
US 2025/0174353 A1      May 29, 2025

Related U.S. Application Data

(60) Provisional application No. 63/302,492, filed on Jan. 24, 2022.

(51) Int. Cl.
*G16H 50/20*          (2018.01)
*A61B 8/00*           (2006.01)
(Continued)

(52) U.S. Cl.
CPC ........... *G16H 50/20* (2018.01); *A61B 8/0825* (2013.01); *A61B 8/085* (2013.01); *A61B 8/5207* (2013.01);
(Continued)

(58) Field of Classification Search
None
See application file for complete search history.

(56) References Cited

U.S. PATENT DOCUMENTS

2016/0120502 A1* 5/2016 Sadeghi-Naini ....... G16H 50/30
600/443
2018/0189947 A1* 7/2018 Tadayyon .............. A61B 8/085

FOREIGN PATENT DOCUMENTS

WO     2014186899 A1    11/2014
WO     2016205936 A1    12/2016
(Continued)

OTHER PUBLICATIONS

NPL_51_M. Byra, A. Nowicki, H. Wroblewska-Piotrzkowska, and K. Dobruch-Sobczak, "Classification of breast lesions using segmented quantitative ultrasound maps of homodyned K distribution parameters," Med. Phys., vol. 43, No. 10, pp. 5561-5569, Oct. 2016, doi: 10.1118/1.4962928.

(Continued)

*Primary Examiner* — Andrew H Lam
(74) *Attorney, Agent, or Firm* — Whiteford, Taylor & Preston, LLP; Peter J. Davis

(57)          ABSTRACT

A system for predicting breast cancer response to neo-adjuvant chemotherapy (NAC) using quantitative ultrasound (QUS) parametric images and/or B-mode images, the system comprising: an imaging system for acquiring at least one ultrasound data frame comprising a raw RF signal, and/or an image; with a computer system performing the operations of: receiving the at least one ultrasound data (Continued)

frame and using one or more predefined rules to identify a region of interest (ROI) in each of the at least one ultrasound data frame; generating at least one quantitative ultrasound (QUS) parametric map and/or processed B-mode image for the tumor; with a feature network of a machine learning architecture, extracting optimal feature maps from the QUS parametric images and/or B-mode images; and classifying the tumor subject into a responder or a non-responder to the NAC.

21 Claims, 6 Drawing Sheets

(51) Int. Cl.
| | |
|---|---|
| *A61B 8/08* | (2006.01) |
| *G06T 7/00* | (2017.01) |
| *G06V 10/25* | (2022.01) |
| *G06V 10/764* | (2022.01) |
| *G06V 10/77* | (2022.01) |
| *G06V 10/774* | (2022.01) |
| *G06V 10/82* | (2022.01) |
| *G16H 30/40* | (2018.01) |

(52) U.S. Cl.
CPC ............ *G06T 7/0012* (2013.01); *G06V 10/25* (2022.01); *G06V 10/764* (2022.01); *G06V 10/7715* (2022.01); *G06V 10/774* (2022.01); *G06V 10/82* (2022.01); *G16H 30/40* (2018.01); *G06T 2207/10132* (2013.01); *G06T 2207/20081* (2013.01); *G06T 2207/20084* (2013.01); *G06T 2207/30068* (2013.01); *G06T 2207/30096* (2013.01); *G06V 2201/03* (2022.01)

(56) References Cited

FOREIGN PATENT DOCUMENTS

| WO | 2021195221 A1 | 9/2021 |
|---|---|---|
| WO | 2022266774 A1 | 12/2022 |

OTHER PUBLICATIONS

NPL_52_J. Wu, G. Gong, Y. Cui, and R. Li, "Intratumor partitioning and texture analysis of dynamic contrast-enhanced (DCE)-MRI identifies relevant tumor subregions to predict pathological response of breast cancer to neoadjuvant chemotherapy," J. Magn. Reson. Imaging, vol. 44, No. 5, pp. 1107-1115, Nov. 2016, doi: 10.1002/jmri.25279.

NPL_53_A. Sadeghi-Naini et al., "Early detection of chemotherapy-refractory patients by monitoring textural alterations in diffuse optical spectroscopic images," Med. Phys., vol. 42, No. 11, pp. 6130-6146, Nov. 2015, doi: 10.1118/1.4931603.

NPL_54_E. Karami et al., "Quantitative MRI Biomarkers of Stereotactic Radiotherapy Outcome in Brain Metastasis," Sci. Rep., vol. 9, No. 19830, Dec. 2019, doi: 10.1038/s41598-019-56185-5.

NPL_55_A. M. Fowler, D. A. Mankoff, and B. N. Joe, "Imaging Neoadjuvant Therapy Response in Breast Cancer," Radiology, vol. 285, No. 2, pp. 358-375, Nov. 2017, doi: 10.1148/radiol. 2017170180.

NPL_1_H. Sung et al., "Global cancer statistics 2020: GLOBOCAN estimates of incidence and mortality worldwide for 36 cancers in 185 countries," CA. Cancer J. Clin., Feb. 2021, doi: 10.3322/caac. 21660.

NPL_2_F. Bray, J. Ferlay, I. Soerjomataram, R. L. Siegel, L. A. Torre, and A. Jemal, "Global cancer statistics 2018: GLOBOCAN estimates of incidence and mortality worldwide for 36 cancers in 185 countries," CA. Cancer J. Clin., vol. 68, No. 6, pp. 394-424, Nov. 2018, doi: 10.3322/caac.21492.

NPL_3_S.H. Giordano, "Update on Locally Advanced Breast Cancer," Oncologist, vol. 8, No. 6, pp. 521-530, Dec. 2003, doi: 10.1634/theoncologist. 8-6-521.

NPL_4_G.N. Hortobagyi, "Comprehensive management of locally advanced breast cancer.," Cancer, vol. 66, No. 6 Suppl, pp. 1387-1391, Sep. 1990, doi: 10.1002/1097¬0142(19900915)66:14+ <1387:: aid-cncr2820661414>3.0.co;2-i.

NPL_5_G. Gardin et al., "Locally advanced non-metastatic breast cancer: analysis of prognostic factors in 125 patients homogeneously treated with a combined modality approach," Eur. J. Cancer, vol. 31A, No. 9, pp. 1428-1433, 1995, doi: 10.1016/0959-8049(95)00199-S.

NPL_6_S. J. Cleator, A. Makris, S. E. Ashley, R. Lal, and T. J. Powles, "Good clinical response of breast cancers to neoadjuvant chemoendocrine therapy is associated with improved overall survival.," Ann. Oncol. Off. J. Eur. Soc. Med. Oncol., vol. 16, No. 2, pp. 267-272, Feb. 2005, doi: 10.1093/annonc/mdi049.

NPL_7_B. T. Hennessy et al., "Outcome after pathologic complete eradication of cytologically proven breast cancer axillary node metastases following primary chemotherapy," J. Clin. Oncol., vol. 23, No. 36, pp. 9304-9311, 2005, doi: 10.1200/JCO.2005.02.5023.

NPL_8_J. B. Nikas, W. C. Low, and P. A. Burgio, "Prognosis of treatment response (pathological complete response) in breast cancer," Biomark. Insights, vol. 7, pp. 59-70, May 2012, doi: 10.4137/BMI.S9387.

NPL_9_D. Sethi, R. Sen, J. Sen, S. Parshad, S. Khetarpal, and M. Garg, "Histopathologic changes following neoadjuvant chemotherapy in various malignancies," Int. J. Appl. Basic Med. Res., vol. 2, No. 2, p. 111, 2012, doi: 10.4103/2229-516x.106353.

NPL_10_W. Hague, V. Verma, S. Hatch, V. Suzanne Klimberg, E. Brian Butler, and B. S. Teh, "Response rates and pathologic complete response by breast cancer molecular subtype following neoadjuvant chemotherapy," Breast Cancer Res. Treat., vol. 170, No. 3, pp. 559-567, Aug. 2018, doi: 10.1007/s10549-018-4801-3.

NPL_11_K. Brindle, "New approaches for imaging tumour responses to treatment," Nature Reviews Cancer, vol. 8, No. 2. pp. 94-107, Feb. 2008, doi: 10.1038/nrc2289.

NPL_12_G. Von Minckwitz et al., "Neoadjuvant Chemotherapy Adapted by Interim Response Improves Overall Survival of Primary Breast Cancer Patients—Results of the GeparTrio Trial"/ Cancer Research, (2011) 71 (24_Supplement): s3-2, doi: 10.1158/0008-5472.SABCS11-S3-2, Abstract, 1 page.

NPL_13_G. Von Minckwitz et al., "Neoadjuvant vinorelbine-capecitabine versus docetaxel-doxorubicin-cyclophosphamide in early nonresponsive breast cancer: Phase III randomized gepartrio trial,"/ Natl. Cancer Inst. , vol. 100, No. 8, pp. 542-551, Apr. 2008, doi: 10.1093/jnci/djn085.

NPL_14_M. Yang, T. M. Krueger, J. G. Miller, and M. R. Holland, "Characterization anisotropic myocardial backscatter using spectral slope, intercept and midband fit parameters," Ultrason. Imaging, vol. 29, No. 2, pp. 122-134, Apr. 2007, doi: 10.1177/016173460702900204.

NPL_15_D. J. Coleman, F. L. Lizzi, R. H. Silverman, L. Helson, J. H. Torpey, and M. J. Rondeau, "A model for acoustic characterization of intraocular tumors.," Invest. Ophthalmol. Vis. Sci., vol. 26, No. 4, pp. 545-550, Apr. 1985.

NPL_16_H. Tadayyon, A. Sadeghi-Naini, L. Wirtzfeld, F. C. Wright, and G. Czarnota, "Quantitative ultrasound characterization of locally advanced breast cancer by estimation of its scatterer properties," Med. Phys., vol. 41, No. 012903, Jan. 2014, doi: 10.1118/1. 4852875.

NPL_17_H. Tadayyon, A. Sadeghi-Naini, and G. Czarnota, "Non-invasive Characterization of Locally Advanced Breast Cancer Using Textural Analysis of Quantitative Ultrasound Parametric Images," Translational Oncology, vol. 71, No. 6, Dec. 2014, pp. 759-767.

NPL_18_A. Sadeghi-Naini et al., "Quantitative ultrasound spectroscopic imaging for characterization of disease extent in prostate cancer patients," Transl. Oncol., vol. 8, No. 1, pp. 25-34, Feb. 2015, doi: 10.1016/j.tranon.2014.11.005.

NPL_19_B. Banihashemi, R. Vlad, B. Debeljevic, A. Giles, M. C. Kolios, and G. J. Czarnota, "Ultrasound imaging of apoptosis in

(56)                    References Cited

OTHER PUBLICATIONS tumor response: Novel preclinical monitoring of photodynamic therapy effects," Cancer Res., vol. 68, No. 20, pp. 8590-8596, Oct. 2008, doi: 10.1158/0008-5472.CAN-08-0006.

NPL_20_R. M. Vlad, S. Brand, A. Giles, M. C. Kolios, and G. J. Czarnota, "Quantitative ultrasound characterization of responses to radiotherapy in cancer mouse models," Clin. Cancer Res., vol. 15, No. 6, pp. 2067-2075, Mar. 2009, doi: 10.1158/1078-0432.CCR-08-1970.

NPL_21_G. J. Czarnota et al., "Tumor radiation response enhancement by acoustical stimulation of the vasculature," Proc. Natl. Acad. Sci. U S. A., vol. 109, No. 30, pp. E2033-E2041, Jul. 2012, doi: 10.1073/pnas.1200053109.

NPL_22_A. Sadeghi-Naini et al., "Low-frequency quantitative ultrasound imaging of cell death in vivo," Med. Phys., vol. 40, No. 8, p. 082901, Jul. 2013, doi: 10.1118/1.4812683.

NPL_23_H. Tadayyon et al., "Quantitative ultrasound assessment of breast tumor response to chemotherapy using a multi-parameter approach," Oncotarget, vol. 7, No. 29, pp. 45094¬45111, Jul. 2016, doi: 10.18632/oncotarget.8862.

NPL_24_L. Sannachi et al., "Non-invasive evaluation of breast cancer response to chemotherapy using quantitative ultrasonic backscatter parameters," Med. Image Anal., vol. 20, No. 1, pp. 224-236, Feb. 2015, doi: 10.1016/j.media.2014.11.009.

NPL_25_A. Sadeghi-Naini et al., "Quantitative ultrasound evaluation of tumor cell death response in locally advanced breast cancer patients receiving chemotherapy," Clin. Cancer Res., vol. 19, No. 8, pp. 2163-2173, Feb. 2013, doi: 10.1158/1078-0432.CCR-12-2965.

NPL_26_D. DiCenzo et al., "Quantitative ultrasound radiomics in predicting response to 24 neoadjuvant chemotherapy in patients with locally advanced breast cancer: Results from multi-institutional study," Cancer Med., vol. 9, No. 16, pp. 5798-5806, Aug. 2020, doi: 10.1002/cam4. 3255.

NPL_27_A. Sadeghi-Naini et al., "Conventional frequency ultrasonic biomarkers of cancer treatment response in vivo," Transl. Oncol., vol. 6, No. 3, pp. 234-243, 2013, doi: 10.1593/t1o.12385.

NPL_28_A. Sadeghi-Naini et al., "Chemotherapy-Response Monitoring of Breast Cancer Patients Using Quantitative Ultrasound-Based Intra-Tumour Heterogeneities," Sci. Rep., vol. 7, No. 10352, Dec. 2017, doi: 10.1038/s41598-017-09678-0.

NPL_29_A. Sadeghi-Naini et al., "Early prediction of therapy responses and outcomes in breast cancer patients using quantitative ultrasound spectral texture," Oncotarget, vol. 5, No. 11, pp. 3497-3511, 2014, doi: 10.18632/oncotarget.1950.

NPL_30_A. Dasgupta et al., "Quantitative ultrasound radiomics using texture derivatives in prediction of treatment response to neo-adjuvant chemotherapy for locally advanced breast cancer," Oncotarget, vol. 11, No. 42, pp. 3782-3792, Oct. 2020, doi: 10.18632/oncotarget.27742.

NPL_31_H. Tadayyon et al., "A priori Prediction of Neoadjuvant Chemotherapy Response and Survival in Breast Cancer Patients using Quantitative Ultrasound," Sci. Rep., vol. 7, No. 45733 (2017), Apr. 2017, doi: 10.1038/srep45733.

NPL_32_D. Shen, G. Wu, and H.-I. Suk, Deep Learning in Medical Image Analysis. Elsevier, 2017.

NPL_33_G. Litj ens et al., "A survey on deep learning in medical image analysis," Medical Image Analysis, vol. 42. pp. 60-88, Dec. 1, 2017, doi: 10.1016/j.media.2017.07.005.

NPL_34_K. Ravichandran, N. Braman, A. Janowczyk, and A. Madabhushi, "A deep learning classifier for prediction of pathological complete response to neoadjuvant chemotherapy from baseline breast DCE-MRI," in Medical Imaging 2018: Computer Aided Diagnosis, 2018, vol. 10575, p. 11, doi: 10.1117/12.2294056.

NPL_35_Y. Qu, H. Zhu, K. Cao, X. Li, M. Ye, and Y. Sun, "Prediction of pathological complete response to neoadjuvant chemotherapy in breast cancer using a deep learning (DL) method," Thorac. Cancer, vol. 11, No. 3, pp. 651-658, Mar. 2020, doi: 10.1111/1759¬7714.13309.

NPL_36_R. Ha et al., "Prior to Initiation of Chemotherapy, Can We Predict Breast Tumor Response? Deep Learning Convolutional Neural Networks Approach Using a Breast MRI Tumor Dataset," I Digit. Imaging, vol. 32, No. 5, pp. 693-701, Oct. 2019, doi: 10.1007/s10278-018-0144-1.

NPL_37_F. Wang et al., "Residual Attention Network for Image Classification," Proc.—30th IEEE Conf. Comput. Vis. Pattern Recognition, CVPR 2017, vol. Jan. 2017, pp. 6450-6458, Apr. 2017.

NPL_38_K. He, X. Zhang, S. Ren, and J. Sun, "Deep residual learning for image recognition," in Proceedings of the IEEE Computer Society Conference on Computer Vision and Pattern Recognition, 2016, vol. Dec. 2016, pp. 770-778, doi: 10.1109/CVPR. 2016.90.

NPL_39_E. A. A. Eisenhauer et al., "New response evaluation criteria in solid tumours: Revised RECIST guideline (version 1.1)," Eur J Cancer, No. 14865, pp. 228-247, Jan. 2009, doi: 10.1016/j . ej ca.2008.10. 026.

NPL_40_K. N. Ogston et al., "A new histological grading system to assess response of breast cancers to primary chemotherapy: prognostic significance and survival," The Breast, vol. 12, No. 5, pp. 320-327, Oct. 2003, doi: 10.1016/S0960-9776(03)00106-1.

NPL_41_H. Taleghamar, H. Moghadas-Dastjerdi, G. J. Czarnota, and A. Sadeghi-Naini, "Characterizing intra-tumor regions on quantitative ultrasound parametric images to predict breast cancer response to chemotherapy at pre-treatment," Sci. Rep., vol. 11, No. 14865, Jul. 2021, doi: 10.1038/s41598-021-94004-y.

NPL_42_Y. Labyed, T. A. Bigelow, and B. L. McFarlin, "Estimate of the attenuation coefficient using a clinical array transducer for the detection of cervical ripening in human pregnancy," Ultrasonics, vol. 51, No. 1, pp. 34-39, Jan. 2011, doi: 10.1016/j.ultras.2010.05. 005.

NPL_43_L. X. Yao, J. A. Zagzebski, and E. L. Madsen, "Backscatter coefficient measurements using a reference phantom to extract depth-dependent instrumentation factors," Ultrason. Imaging, vol. 12, No. 1, pp. 58-70, Jan. 1990, doi: 10.1016/0161-7346(90)90221-i.

NPL_44_M. F. Insana, R. F. Wagner, D. G. Brown, and T. J. Hall, "Describing small-scale structure in random media using pulse-echo ultrasound," J Acoust. Soc. Am., vol. 87, No. 1, pp. 179-192, Jan. 1990.

NPL_45_M. L. Oelze, W. D. O'Brien, J. P. Blue, and J. F. Zachary, "Differentiation and characterization of rat mammary fibroadenomas and 4T1 mouse carcinomas using quantitative ultrasound imaging," IEEE Trans. Med. Imaging, vol. 23, No. 6, pp. 764¬771, Jun. 2004, doi: 10.1109/TMI.2004.826953.

NPL_46_A. Sadeghi-Naini et al., "Breast-Lesion Characterization using Textural Features of Quantitative Ultrasound Parametric Maps," Sci. Rep., vol. 7, No. 13638, Dec. 2017, doi: 10.1038/S41598-017-13977-X.

NPL_47_K. A. Topp, J. F. Zachary, and J. O'Brien, "Quantifying B-mode images of in vivo rat mammary tumors by the frequency dependence of backscatter," J Ultrasound Med , vol. 20, No. 6, pp. 605-612, 2001, doi: 10.7863/JUM.2001.20.6.605.

NPL_48_D. P. Kingma and J. L. Ba, "Adam: A method for stochastic optimization," in 3rd International Conference on Learning Representations, ICLR 2015—Conference Track Proceedings, 2015.

NPL_49_L. M. Zintgraf, T. S. Cohen, T. Adel, and M. Welling, "Visualizing Deep Neural Network Decisions: Prediction Difference Analysis," 5th Int. Conf. Learn. Represent. ICLR 2017—Conf. Track Proc., Feb. 2017.

NPL_50_L. Sannachi et al., "Response monitoring of breast cancer patients receiving neoadjuvant chemotherapy using quantitative ultrasound, texture, and molecular features," PLoS One, vol. 13, No. 1, p. e0189634, Jan. 2018, doi: 10.1371/journal.pone.0189634.

* cited by examiner

16

40          41          18          42

20

Processor     GPU     Memory

GUI

45

AI Gateway

I/O Module

43

46          44          18

Server

46

Imaging
System

14

10

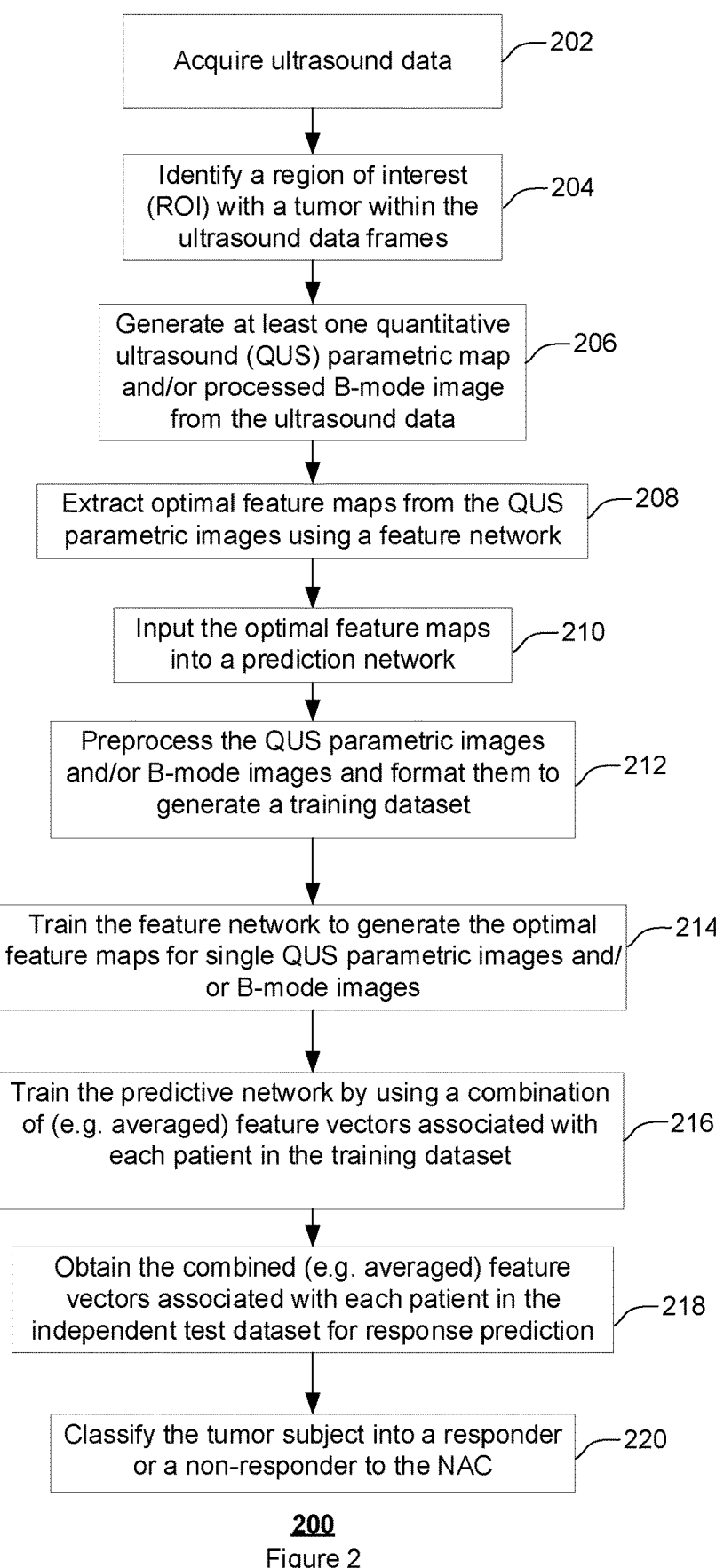

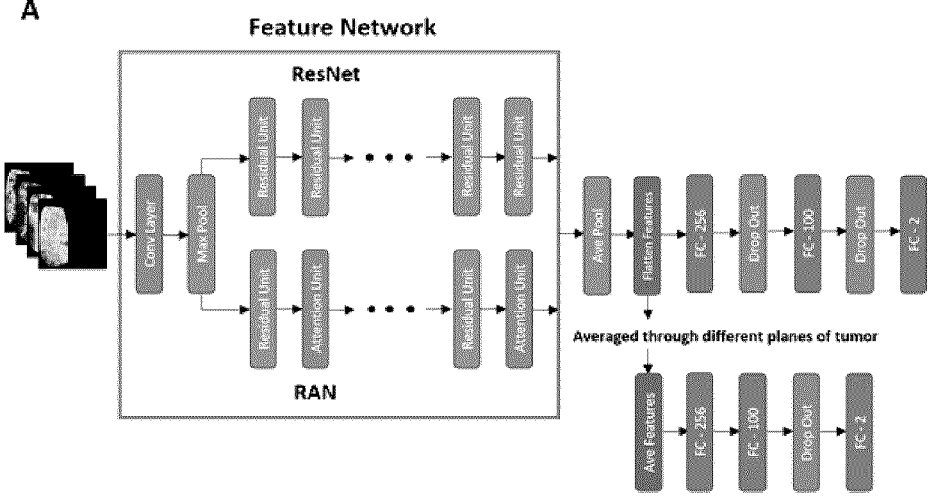
Figure 3a
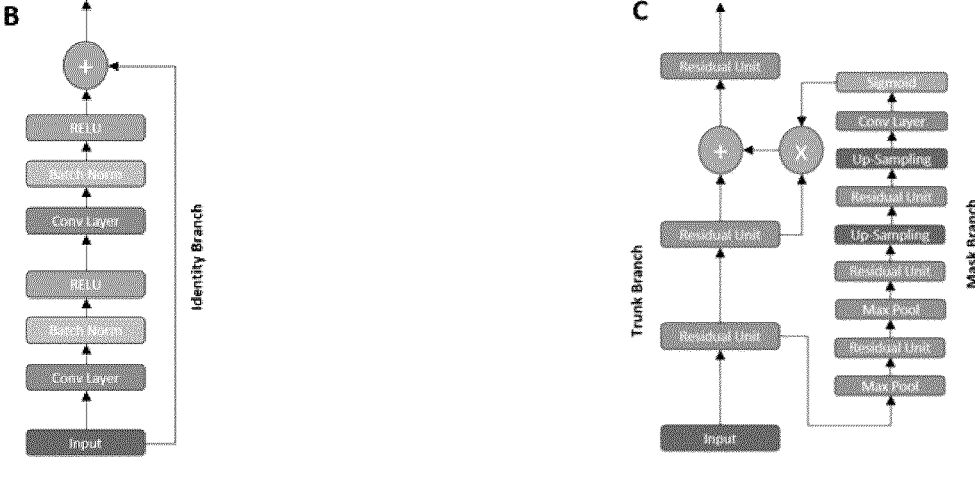
Figure 3b                            Figure 3c

Responder

Non-Responder

Responder
Non-Responder
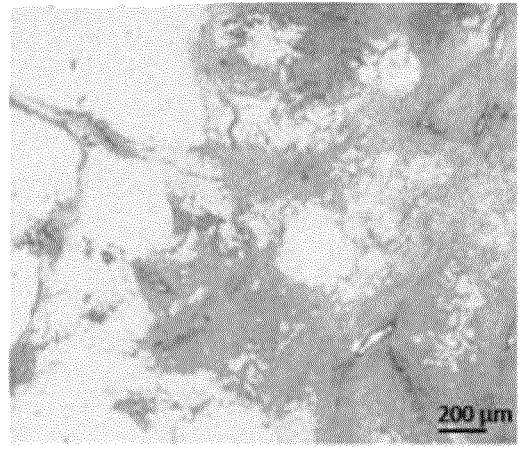
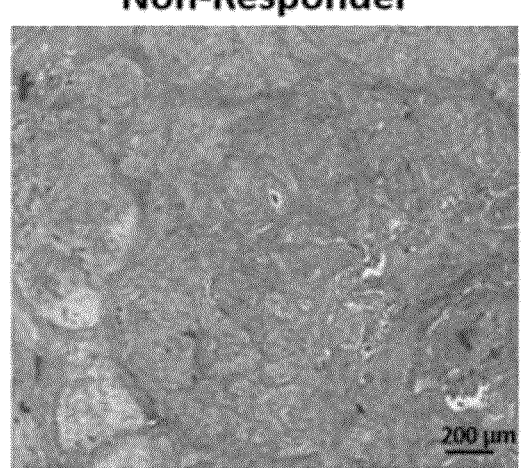
Figure 5a
Figure 5b
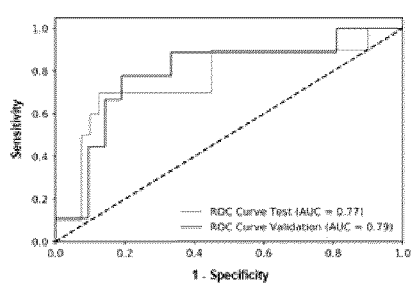
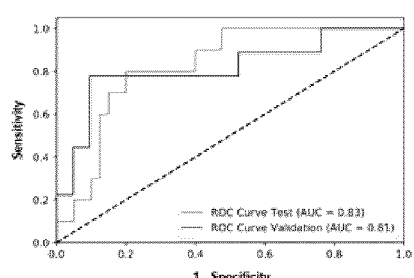
Figure 6a
Figure 6b
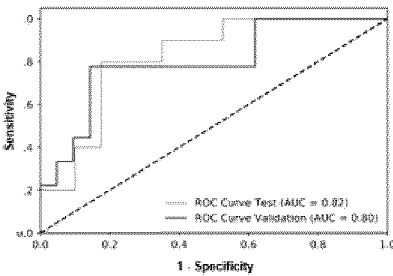
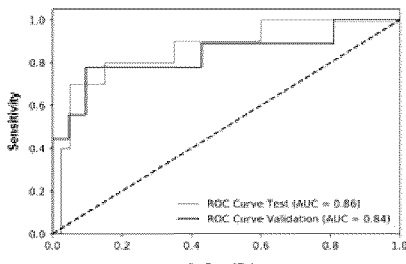
Figure 6c
Figure 6d

DEEP LEARNING OF QUANTITATIVE ULTRASOUND MULTI-PARAMETRIC IMAGES AT PRE-TREATMENT TO PREDICT BREAST CANCER RESPONSE TO CHEMOTHERAPY

FIELD

The present disclosure relates to deep learning-based methodology to predict breast cancer response to neo-adjuvant chemotherapy (NAC) using the quantitative ultrasound (QUS) multi-parametric imaging at pre-treatment.

BACKGROUND

Breast cancer is the most common cancer type and the foremost cause of cancer-related death among women [1], [2]. In 2020, around 2.3 million new cases of breast cancer were diagnosed worldwide and it caused around 0.7 million deaths among females [1]. Locally advanced breast cancer (LABC) is an aggressive subtype of breast cancer that includes up to 20% of new cases each year [3]. LABC is often identified with tumors greater than 5 cm in size and possibly with skin and/or chest wall involvement. Moreover, LABC includes patients diagnosed with inflammatory breast cancer or multiple positive axillary lymph nodes [3][4].

Patients diagnosed with LABC suffer from high risk of relapse and metastasis with a local recurrence rate of about 48% in 5 years [5]. With availability of different systemic and targeted regimens, neoadjuvant chemotherapy (NAC) followed by surgery is currently considered as the standard treatment for LABC patients [6]-[9]. In some cases, the surgery is followed by adjuvant radiation and/or hormonal therapies to reduce the risk of cancer recurrence [4][6]. Although response to NAC has demonstrated a high correlation to the patient survival, complete pathological response is limited to less than 30% of the patients, with about 30% of the patient do not even partially respond to NAC [3], [4], [6], [10]-[15]. To determine the tumor pathological response to NAC, post-surgical histopathology is considered as the standard approach [6]-[9]. However, post-surgical evaluations cannot be used for adjusting the NAC or switching to salvage treatment.

Currently, monitoring tumor response to NAC mostly relies on physical examination or standard anatomical imaging to assess the changes in tumor size. The main limitation of these methods is that detectable changes in tumor dimensions usually become apparent after several months of therapy, and in some cases a measurable change may not become evident on imaging despite a pathological response to NAC [16]. Early prediction of tumor response to NAC can permit therapy adjustments by modifying the regimen, dose, and/or sequence of treatment options, switching to more effective treatments or even salvage therapies before it is potentially too late for individual patients [17], [18]. A personalized strategy for LABC treatment is anticipated to improve tumor response to neoadjuvant therapies, spare patients from unnecessary side effects of ineffective treatment, and improve their overall survival and quality of life.

Ultrasound is a portable, rapid and cost-efficient imaging modality that can be applied to characterize tissue physical properties without injection of any exogenous contrast agents. In particular, quantitative ultrasound (QUS) techniques have been introduced to derive quantitative measures of tissue biophysical properties that are independent of instrument settings, with a lower level of dependence to the operator [19]. Quantitative ultrasound spectral analysis techniques examine the frequency dependence of the ultrasound radiofrequency (RF) signal backscattered from the underlying tissue which can be used for tissue micro-structure characterization [19]. The QUS parameters derived from the analysis of normalized power spectrum of RF signal including the mid-band fit (MBF), spectral slope (SS), spectral 0-MHz intercept (SI), effective scatterer diameter (ESD) and effective acoustic concentration (EAC) have shown promises in detecting and characterizing malignancies, examination of liver tissues and detecting cardiovascular disease [20]-[26].

It has been shown that QUS spectral parameters can detect tumor cell death induced by various anti-cancer-therapies [27]-[30]. Also, several studies have demonstrated that the hand-crafted features derived from the QUS parametric maps can be used to predict and monitor breast cancer response to neoadjuvant chemotherapy before or within weeks after the start of treatment, with a high correlations to clinical and pathological response identified at the end of the treatment [31]-[34]. For example, it has been demonstrated that textural features of QUS spectral parametric maps have higher correlations to histological tumor cell death in response to chemotherapy in comparison with QUS mean-value parameters [35]. Further, A few studies have revealed the potential of the textural features of QUS parametric images in predicting LABC tumor response to NAC as early as one week after starting the treatment [36]-[38]. In a recent study, Tadayyon et al. have demonstrated that using the QUS hand-crafted features derived from both the tumor core and its margin could improve the performance of tumor response prediction before starting the treatment [39].

The deep learning approaches have recently been investigated in different applications of medical image analysis [40], [41]. Such methodologies can potentially remove the process of extracting carefully designed hand-crafted features from images required for conventional machine learning techniques. Instead, the deep learning frameworks optimize their data-driven feature maps during the iterative training procedure [42]. In this context, a few studies have been conducted on adapting deep convolutional neural networks (DCNN) for NAC therapy response prediction in breast cancer patients using magnetic resonance imaging (MRI) [43]-[45]. Moreover, few studies have explored the potential of DCNNs in analyzing ultrasound images of breast tumors for cancer classification. For example, Byra et al. have demonstrated the potential of convolutional neural networks for breast lesion classification using Nakagami parametric images [46]. No previous study has explored the efficacy of deep learning techniques with QUS multi-parametric images for therapy response prediction.

SUMMARY

In one of aspect of the disclosure, there is provided a system for predicting breast cancer response to neo-adjuvant chemotherapy (NAC) using quantitative ultrasound (QUS) parametric images and/or B-mode images, the system comprising:

an imaging system for acquiring at least one ultrasound data frame comprising a raw RF signal, and/or an image;

a computer system comprising a hardware processor and a memory device on which instructions are encoded to cause the hardware processor to perform the operations of:

receiving the at least one ultrasound data frame and using one or more predefined rules to identify a region of interest (ROI) in each of the at least one ultrasound data frame, the ROI comprising a tumor, and the ROI may be identified automatically;

generating, from the at least one ultrasound data frame at least one quantitative ultrasound (QUS) parametric map and/or processed B-mode image for the tumor;

with a feature network of a machine learning architecture, extracting optimal feature maps from the QUS parametric images and/or B-mode images;

inputting the optimal feature maps into a prediction network of the machine learning architecture, the optimized feature maps obtained from the feature network are combined or averaged over all images associated with each tumor, the feature and prediction networks may be integrated in an end-to-end system, preprocessing the QUS parametric images and/or B-mode images and formatting them to generate a training dataset for a deep learning model, training the feature network to generate the optimal feature maps for single QUS parametric images and/or B-mode images;

training the predictive network by using a combination of, or averaged, feature vectors associated with each patient in the training dataset, in case of an end-to-end system mentioned above, the integrated feature and prediction networks are trained together; and classifying the tumor subject into a responder or a non-responder to the NAC, and classifying a response to as at least one of a complete response, partial response, stable disease, or progressive disease.

In another of its aspects, there is provided a method for predicting a response to neo-adjuvant chemotherapy (NAC) using quantitative ultrasound (QUS) parametric images, the method comprising:

with an imaging system, acquiring at least one ultrasound data frame comprising a raw RF signal, and/or an image;

with a computer system comprising a hardware processor and a memory device on which instructions are encoded to cause the hardware processor performing the operations of:

receiving the at least one ultrasound data frame and using one or more predefined rules to identify a region of interest (ROI) in each of the at least one ultrasound data frame, the ROI comprising a tumor, and the ROI may be identified automatically;

generating, from the at least one ultrasound data frame at least one quantitative ultrasound (QUS) parametric map and/or processed B-mode image for the tumor;

with a feature network of a machine learning architecture, extracting optimal feature maps from the QUS parametric images and/or B-mode images;

inputting the optimal feature maps into a prediction network of the machine learning architecture, the optimized feature maps obtained from the feature network are combined or averaged over all images associated with each tumor, the feature and prediction networks may be integrated in an end-to-end system, preprocessing the QUS parametric images and/or B-mode images and formatting them to generate a training dataset for a deep learning model, training the feature network to generate the optimal feature maps for single QUS parametric images and/or B-mode images;

training the predictive network by using a combination of, or averaged, feature vectors associated with each patient in the training dataset, in case of an end-to-end system mentioned above, the integrated feature and prediction networks are trained together; and classifying the tumor subject into a responder or a non-responder to the NAC, and classifying a response to as at least one of a complete response, partial response, stable disease, or progressive disease.

Advantageously, there is provided a novel deep learning-based methodology for predicting breast cancer response to neo-adjuvant chemotherapy (NAC) using the quantitative ultrasound (QUS) multi-parametric imaging at pre-treatment. The machine learning architecture comprises one of a deep convolutional neural network (DCNN) architecture, a deep learning architecture, and a transformer architecture.

BRIEF DESCRIPTION OF THE DRAWINGS

FIG. 2 shows a flowchart outlining exemplary steps for breast cancer response to neo-adjuvant chemotherapy (NAC) using the quantitative ultrasound (QUS) multi-parametric imaging at pre-treatment;

FIG. 3a shows a scheme of a deep learning framework for response prediction, demonstrating feature and predictive networks;

FIG. 3b shows a scheme of a deep learning framework for response prediction, demonstrating residual module;

FIG. 3c shows a scheme of a deep learning framework for response prediction, demonstrating attention module;

FIGS. 5a and 5b show histopathology images of surgical specimens obtained from representative patients;

FIGS. 6a-d show ROC curves generated for responding and non-responding patients in the validation set and independent test set identified at pre-treatment using the predictive models 1-4 in Table 2.

DETAILED DESCRIPTION OF EXEMPLARY EMBODIMENTS

Figure 1:
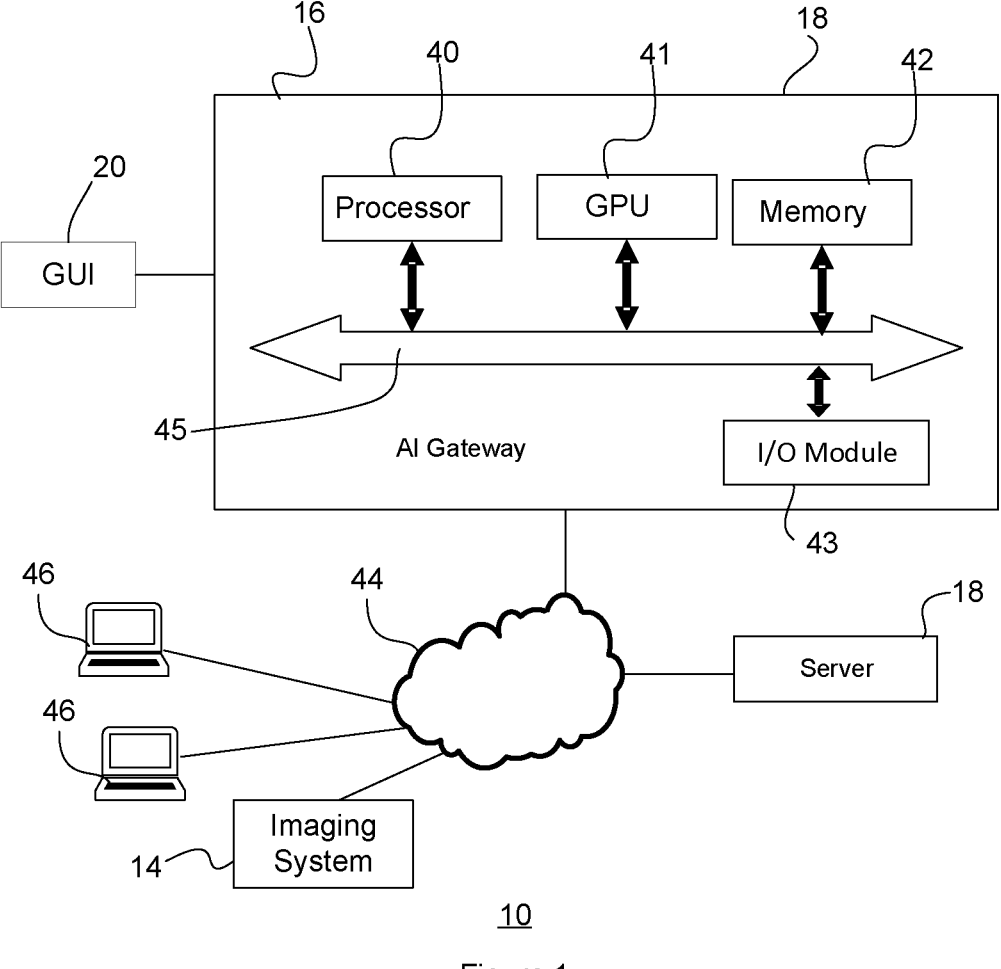
FIG. 1 shows a top-level diagram of an overall system architecture 10 for predicting breast cancer response to neo-adjuvant chemotherapy (NAC) using the quantitative ultrasound (QUS) multi-parametric imaging at pre-treatment.

The following detailed description refers to the accompanying drawings. Wherever possible, the same reference numbers are used in the drawings and the following description to refer to the same or similar elements. While embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims.

Moreover, it should be appreciated that the particular implementations shown and described herein are illustrative of the invention and are not intended to otherwise limit the scope of the invention in any way. Indeed, for the sake of brevity, certain sub-components of the individual operating components, and other functional aspects of the systems may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

Referring to FIG. 1, there is shown a top-level diagram of an overall system architecture 10 for predicting breast cancer response to neo-adjuvant chemotherapy (NAC) using the quantitative ultrasound (QUS) multi-parametric imaging at pre-treatment. The images may be acquired from one or more imaging systems 14 and may comprise medical imaging equipment such as a X-ray imaging system, a CT scan imaging system, an ultrasound imaging system, a MRI imaging system, a nuclear medicine imaging system, and so forth. The images 12 captured by the one or more imaging systems 14 are rendered as a digital representation and stored in a computing device 16. The computing device 16 may comprise one or more processing units, such as, graphics processing units (GPUs). In one example, the computing device 16 implements models to predict breast cancer response to neo-adjuvant chemotherapy (NAC), and output the results via a graphical user interface 20 or a customized plug-in on a peripheral screen.

The computing device 16 comprises an image repository 30 for storage of the images 12. The image repository 30 may be computer readable medium e.g. a hard disk. Alternatively, the acquired images 14 may be stored on a storage server 18 or a computing cloud. The image repository 30 may also include images of patients for analysis, and/or training images that have been previously analyzed and/or annotated.

The term computing device refers to data processing hardware and encompass all kinds of apparatus, devices, and machines for processing data, including by way of example, a programmable processor, a computer, or multiple processors or computers. The apparatus can also be, or further include, special purpose logic circuitry, e.g., a central processing unit (CPU) 40, a GPU 41 graphics processing unit); a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. Although a single CPU 40 is illustrated in FIG. 1, two or more processing units may be used according to particular needs, desires, or particular implementations of the computing device 16. Generally, the GPU 41 executes instructions and manipulates data to perform the operations of the computing device 16. In one example, a GPU 41 is implemented to accelerate computations pertaining to the deep learning methodology.

Memory 42 stores data for the computing device 16 and/or other components of the system 10. Although illustrated as a single memory 42 in FIG. 1, two or more memories may be used according to particular needs, desires, or particular implementations of the computing device 16. While memory 42 is illustrated as an integral component of the computing device 16 in alternative implementations, memory 42 can be external to the computing device 16 and/or the system. For example, memory 42 comprises computer-readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically erasable programmable read-only memory (EEPROM), and flash memory devices; magnetic disks, e.g., internal hard disks or removable disks; magneto-optical disks; and CD-ROM, DVD+/-R, DVD-RAM, DVD-ROM disks and Blu-ray disks. The memory 42 may store various objects or data, including caches, classes, frameworks, applications, backup data, jobs, web pages, web page templates, database tables, repositories storing business and/or dynamic information, and any other appropriate information including any parameters, variables, algorithms, models, instructions, rules, constraints, or references thereto. Additionally, the memory may include any other appropriate data, such as logs, policies, security or access data, reporting files, as well as others. The processor 40 and the memory 42 can be supplemented by, or incorporated in, special purpose logic circuitry.

In one example, an application in memory 42 comprises algorithmic instructions providing functionality according to particular needs, desires, or particular implementations of the computing device 16, particularly with respect to functionality required for processing modelling calculations for predicting breast cancer response to neo-adjuvant chemotherapy (NAC).

The computing device 16 may comprise an input/output module 43, to which an input device, such as a keypad, key board, touch screen, microphone, speech recognition device, other devices that can accept user information, and/or an output device that conveys information associated with the operation of the computing device 16, including digital data, visual and/or audio information, or a GUI 20.

The computing device 16 comprises an interface, as part of the I/O module 43, used according to particular needs, desires, or particular implementations of the computing device 16. The interface is used by computing device 16 for communicating with other systems in a distributed environment, connected to network 44. Generally, the interface comprises logic encoded in software and/or hardware in a suitable combination and operable to communicate with the network 44. More specifically, the interface may comprise software supporting one or more communication protocols associated with communications. The various components of the computing system are connected by an interconnections means 45, such as an address bus, data bus, a control bus and a peripheral bus.

Client terminals 46 (e.g., remotely located radiology workstations) may request services related to predicting breast cancer response to neo-adjuvant chemotherapy (NAC) and access the results over the communications network 44. Accordingly, the computing device 16 may provide software as a service (SaaS) to the client terminals 46, or provide an application for local download to the client terminals 46, and/or provide functions using a remote access session to the client terminals 46, such as through a web browser. Accordingly, the annotated medical data may be accessible for clinicians on an on-demand basis from the client terminals 46. System 10 may also comprise data storage 47, which is configured to maintain one or more datasets, including data structures storing linkages and other data, such as medical images, libraries, models and rules. Data storage 47 may be a relational database, a flat data storage, a non-relational database, among others.

In one study, the effectiveness of DCNN methodologies on QUS spectral multi-parametric images was investigated to predict LABC response to NAC before the start of treatment. The QUS spectral parametric images were generated using the ultrasound data acquired from 181 LABC patients at pre-treatment. The patient responses to NAC were identified after their surgery using the standard clinical and pathological criteria, and used as the ground truth to evaluate the performance of the prediction models. The dataset was randomly partitioned into a training set and an independent test set. Different DCNN architectures including RAN [47], and ResNet [48] were investigated for feature extraction in the developed framework. In a set of experiments, the feature maps were extracted from the tumor core and the core and its margin. After averaging the features on different tumor cross-sections, a fully connected network was utilized for response prediction.

Study Protocol

The study was conducted following the guidelines and regulations in accordance with institutional research ethics board approval from Sunnybrook Health Sciences Centre (SHSC), Toronto Canada. The study was open to all women aged 18-85, diagnosed with LABC and planned for NAC followed by surgery. After obtaining written informed consent, 181 eligible patients were recruited for the study. A core needle biopsy was done for each patient to confirm the cancer diagnosis and grade the tumor. The initial tumor size was determined for each patient using the magnetic resonance (MR) images of the affected breast. Ultrasound B-mode images and radiofrequency (RF) data were acquired from the patients (in supine position with arms above the head) before the start of NAC, following a standardized protocol. Three experienced sonographers were responsible for ultrasound data acquisition. For NAC, 62.9% of the patients received doxorubicin, cyclophosphamide followed by paclitaxel/docetaxel (AC-T/D), 32.6% were treated with 5-fluorouracil, epirubicin, cyclophosphamide followed by docetaxel (FEC-D), and 4.5% with paclitaxel and cyclophosphamide (TC). The patients with HER2+ tumors also received tratuzumab. Patients were followed up to 10 years after their treatment and their clinical data were recorded for survival analysis. Out of the 181 patients, about 30% (n=50) were randomly selected through a stratified random sampling and kept unseen as an independent test set, and the remaining patients (n=131) were considered as the training set and used to develop and optimize the predictive models.

Clinical and Pathological Response Evaluation

In keeping with the institutional guidelines, all patients had breast surgery after completing their neoadjuvant chemotherapy. Before surgery, the residual tumor size was determined using MRI. Standard histopathology was performed on the surgical specimens to assess the pathological response of tumor to NAC. The specimens were stained with hematoxylin and eosin (H&E) and prepared when possible on whole-mount 5"×7" pathology slides. The mounted slides were digitized using a confocal scanner (TISSUEscope, Huron Technologies, Waterloo, ON). A board-certified pathologist who remained blinded to the study results examined all pathology samples. A modified response (MR) grading system based on response evaluation criteria in solid tumors (RECIST) [49] and histopathological criteria [39] [50] was used to categorize the patients into two groups of responders and non-responders, as before [51]. In the MR grading system, the MR score is defined as follows: MR 1: no reduction in tumor size; MR 2: less than 30% reduction in tumor size; MR 3: between 30% and 90% reduction in tumor size or a very low residual tumor cellularity determined histopathologically; MR 4: more than 90% reduction in tumor; MR 5: no evident tumor and no malignant cells identifiable in sections from the site of the tumor (ductal carcinoma in situ may be present). In this study, patients with a MR score of 1-2 (less than 30% reduction in tumor size) were considered as non-responders, and patients with a MR score 3-5 (more than 30% reduction in tumor or very low residual tumor cellularity) were determined as responders. In keeping with this, 138 and 43 patients were identified as responders and non-responders, respectively.

FIG. 2 shows a flowchart 200 outlining exemplary steps for predicting breast cancer response to neo-adjuvant chemotherapy (NAC) using the quantitative ultrasound (QUS) multi-parametric imaging at pre-treatment.

Data Acquisition

In step 202, ultrasound RF data was acquired using an imaging system 14. For example, the imaging system 14 is an RF-enabled Sonix RP system (Ultrasonix, Vancouver, Canada) and an L14-5/60 transducer. In one example, the transducer is operated at the center frequency of ~6 MHz with a −6 dB bandwidth of 3-8 MHz, and the RF data were acquired with a sampling frequency of 40 MHz and digitized with a 16-bit resolution. For each tumor, the ultrasound data were acquired at four to seven image planes across the breast with approximately 1 cm intervals. The focal depth was set at the center of the tumor depending on the individual patient circumstances. The breast region for ultrasound scanning may be specified by an oncologist who determined the acquisition scan planes via a physical examination of the patient, step 204. In one example, the image size along the lateral and axial directions is 6 cm and 4-6 cm, respectively

QUS Parametric Map Generation

In step 206, quantitative ultrasound (QUS) techniques were used to generate parametric maps to predict and monitor breast cancer response to neoadjuvant chemotherapy. Generating the parametric images, QUS spectral analyses were performed in conjunction with a sliding window analysis (described below) to derive MBF, SI, ESD, and EAC parameters [23], [24]. The mean power spectrum was obtained by averaging over the Fourier transform of the Hanning-gated RF data calculated for every scan line of the analyzed window. The average power spectrum was normalized using a reference phantom method to remove the effects of the system transfer function and transducer beamforming [52], [53]. The reference phantom was composed of 5 to 30 μm diameter glass beads embedded in a homogeneous background of microscopic oil droplets in gelatin (Medical Physics Department, University of Wisconsin, USA). The reference phantom had an attenuation coefficient of 0.576 dB/MHz·cm and a speed of sound parameter of 1488 m/s. The MBF and SI parameters were estimated using a linear regression analysis within the −6 dB bandwidth of the transducer [23], [54], [55]. The ESD and EAC parameters were derived by fitting a spherical Gaussian form factor model to the estimated backscatter coefficient [56], [57].

To generate the QUS parametric maps for each tumor, the tumor core was manually outlined by trained staff under the supervision of expert oncologists on each scan plane using the associated B-mode image. The tumor margin contour was automatically generated with a thickness of 5 mm around the core, based on the observations of a previous study [39]. Next, the parametric maps were generated for all imaging planes of the tumor using a sliding window analysis throughout the entire region of interest (tumor core and margin) with windows of size 2 mm×2 mm and 95% overlap in both lateral and axial direction, where the calculated parameter for each window was assigned to its center. The sliding window size was selected such that it covers sufficient ultrasound wavelengths in the axial direction for spectral analysis while preserving texture in generated parametric maps, with an overlap size to obtain isotropic pixels [58][59].

Deep Learning Model

In step 208, the parametric maps were received by deep learning framework for response prediction. The scheme of an exemplary deep learning framework is shown in FIGS. 3a-c. In one exemplary implementation, the deep learning framework comprises two cascaded networks, including a residual network (ResNet) and residual attention network (RAN) for extracting optimal feature maps from the parametric images, with a fully connected network for response prediction. The features maps were derived from the tumor core only, as well as the core and its margin. The first network is a deep convolutional neural network (DCNN), with several convolutional layers as its backbone, adapted to extract the optimal feature maps from the QUS parametric images and is called the feature network in this paper. Two main architectures including a modified residual network version 101 (ResNet) [48] and a modified residual attention network version 56 (RAN) [47], were investigated in this study as the backbone of the feature network. FIGS. 3a-c show the fully connected layers after the convolutional layers (backbone) in the feature network that are applied in training this network on single parametric images to extract the optimal feature maps for response prediction. FIGS. 3a-c also show the adapted ResNet and RAN architectures with their residual and attention modules. In the residual module applied in the ResNet architecture, the convolutional layer could be skipped through the identity branch. This strategy permits the very deep networks such as ResNet to avoid overfitting and achieve an improved performance on unseen samples. In the attention module applied in the RAN architecture, the trunk branch determines the information that can be passed through the network, whereas the mask branch determines the amount of information from the trunk branch that should be passed. Therefore, the module is able to pass the important information with higher weights and reduce the effect of less-important information in the network's output.

As shown in the FIGS. 3a-c, the optimized feature maps obtained from the feature network are averaged over all parametric images associated with each tumor, and subsequently used in a second fully connected network (predictive network) adapted for response prediction at the patient level (described further below), step 210. The predictive network consists of two fully-connected layers with an input layer with the same size as the flatten feature vector (256), a middle layer with 100 neurons, and a soft max layer at the end with an output size of two to predict the probability of the response categories (responder versus non-responder) for each patient. Drop-out layers have been added after the first and second layer of this network to avoid overfitting and enhance its generalization performance.

Preprocessing and Model Training

Before training the models, the parametric images were preprocessed and adjusted for the convolutional model, step 212. About 25% (31 patients) of the training set was randomly selected as a validation set to optimize the network hyperparameters. The parametric images were resampled to the size of 512×512 pixel. Then the pixel values in the parametric images of the training set were normalized to (0 1) to facilitate the training convergence. The training set normalization parameters were used for normalizing the validation and test sets. In order to improve the network training and alleviate the problem of having a relatively small training dataset, data augmentation was applied on the training set. For augmenting the training data, flipping horizontally and shifting both horizontally and vertically (maximum shift: 30% of image size) were stochastically applied.

Next in step 214, the feature network was trained to generate the optimal feature maps for single QUS parametric images, in the first step of model training. For training the feature network, parametric images of the training set were fed into the network while different imaging planes of each tumor were considered as independent inputs with the tumor response as their output. The optimal feature maps for each imaging plane were acquired by feeding its corresponding parametric images into the trained feature network. For each patient, the optimal feature maps were calculated for all 2D imaging planes of the tumor, flatten to a 1D vector, and subsequently averaged over the entire tumor volume to obtain an averaged feature vector with size of 256×1 that was used in the predictive network. This strategy was applied to standardize the input size of the networks for different tumors with various sizes and, consequently, different number of QUS parametric images. Next, in step 216, the predictive network was trained using the averaged feature vectors associated with the patients in the training set, and evaluated over the independent test set for response prediction. For training the networks, the cross entropy was used as the loss function, with a cost weight ratio of C:1 (C≥1; optimized as described below) for non-responders to responders to account for the unbalance in the dataset. The network hyperparameters including the dropout rate (range: 0.3-0.7), width of the hidden fully connected layers (range: 50-300), learning rate (range: 0.1-0.00001), cost weight (range: $1 \leq C \leq 10$), and batch size (range: 4-16) were optimized using the validation set. Preliminary experiments were conducted using the validation set to select the network training optimizer among the Adam and stochastic gradient descent (SGD) methods, where the Adam optimizer was selected and applied [60]. The optimal hyperparameters for training the models were as follows: dropout rate=0.5, learning rate=0.0001, cost weight=5, batch size=8. Early stopping was used to avoid overfitting by monitoring the network's performance on the validation set during the training process.

Response Prediction and Risk Assessment

In different experiments, the QUS multi-parametric images (MBF, SI, ESD, and EAC) of the tumor core, as well as the core and its margin were investigated, as the inputs to the DCNN framework and their performance were compared in response prediction. The deep learning models with different feature networks were trained and optimized using the training set. The performance of the optimized models was evaluated on the independent test set using the accuracy, sensitivity, specificity, and the ROC analysis, step 218. In this study, sensitivity refers to the ratio of the non-responses that were predicted as non-responder, and specificity refers to the ratio of the responding patients correctly predicted as responder by the model. A prediction difference analysis (PDA) was performed to visualize the importance of different regions of the input QUS parametric images to the network's decision [61]. In each iteration of the modified PDA procedure applied in this study, a small patch (8×8 pixel with 50% overlap between adjacent patches) of one of the input parametric images was occluded (pixel values were set to zero). The absolute change in the model's prediction (output probability) was then calculated compared to the case of inputting the original parametric images, and considered as the impact of the occluded patch on the network's decision, step 220. The PDA maps were generated for each input parametric image by sliding the occluding patch over the image and assigning the estimated impact to its center.

The efficacy of the developed predictive models in differentiating the LABC patients with different recurrence-free survival was assessed through Kaplan-Meier survival analysis. The survival curves were generated for the responders and non-responders identified based on each model's prediction at pre-treatment, and at post-treatment based on the clinical and histopathological criteria. A long-rank test was applied to assess for statistically significant differences between the survival curves of the two response cohorts obtained in each experiment

Results

Table 1 presents the clinical and histopathological characteristics of the participating patients. The patients had an average initial tumor size of 5.2 cm, and an average residual tumor size of 2.5 cm at the end of the treatment. Using the MR grading system, 76.2% and 23.8% of the patients were identified as responders and non-responder, respectively, at the end of the treatment.

TABLE 1

| Patients' characteristics | | | |
|---|---|---|---|
| | Data Set | | |
| | All | Training | Test |
| | | Mean ± SD/Percentage | |
| Characteristic | | | |
| Age | 50.6 ± 11.5 years | 51.2 ± 11.5 years | 49.2 ± 11.4 years |
| Initial Tumor Size | 5.2 ± 2.7 cm | 5.3 ± 2.7 cm | 5.1 ± 2.7 cm |
| Residual Tumor size | 2.5 ± 3.4 cm | 2.8 ± 3.7 cm | 1.9 ± 2.3 cm |
| Histology | | | |
| Invasive Ductal Carcinoma | 90.3% | 89.8% | 91.7% |
| Invasive Lobular Carcinoma | 3.4% | 4.6% | 0.0% |
| Invasive Metaplastic Carcinoma | 6.3% | 5.6% | 8.3% |
| Tumor Grade | | | |
| Grade I | 10.6% | 12.1% | 10% |
| Grade II | 38.8% | 36.4% | 45% |
| Grade III | 50.6% | 51.5% | 45% |
| Molecular Features | | | |
| ER+ | 63.4% | 62.5% | 64.4% |
| PR+ | 54.7% | 55.5% | 51.1% |
| HER2+ | 34.3% | 30.5% | 46.7% |
| Triple Negative | 24.4% | 26.6% | 17.8% |
| ER+/PR+/HER2+ | 18.6% | 18.0% | 20.0% |
| ER+/PR+/HER2− | 33.7% | 35.9% | 26.7% |
| ER−/PR−/HER2+ | 10.5% | 9.4% | 15.5% |

TABLE 1-continued

| | Patients' characteristics | | |
| | | | |
| | | Data Set | |
| | All | Training | Test |
| | | Mean ± SD/Percentage | |
| | | NAC | |
| AC-T/D | 62.9% | 63.2% | 62% |
| FEC-D | 32.6% | 31.2% | 36% |
| TC | 4.5% | 5.6% | 2% |
| | | Therapy Response | |
| Responder | 76.2% | 74.8% | 80% |
| Non-Responder | 23.8% | 25.2% | 20% |

Figures 4A, 4B, 4C, 4D, 4E, 4F, 4G, 4H, 4I, 4J, 4K, 4L, 4M, 4N, 4O, 4P, 4Q, 4R:
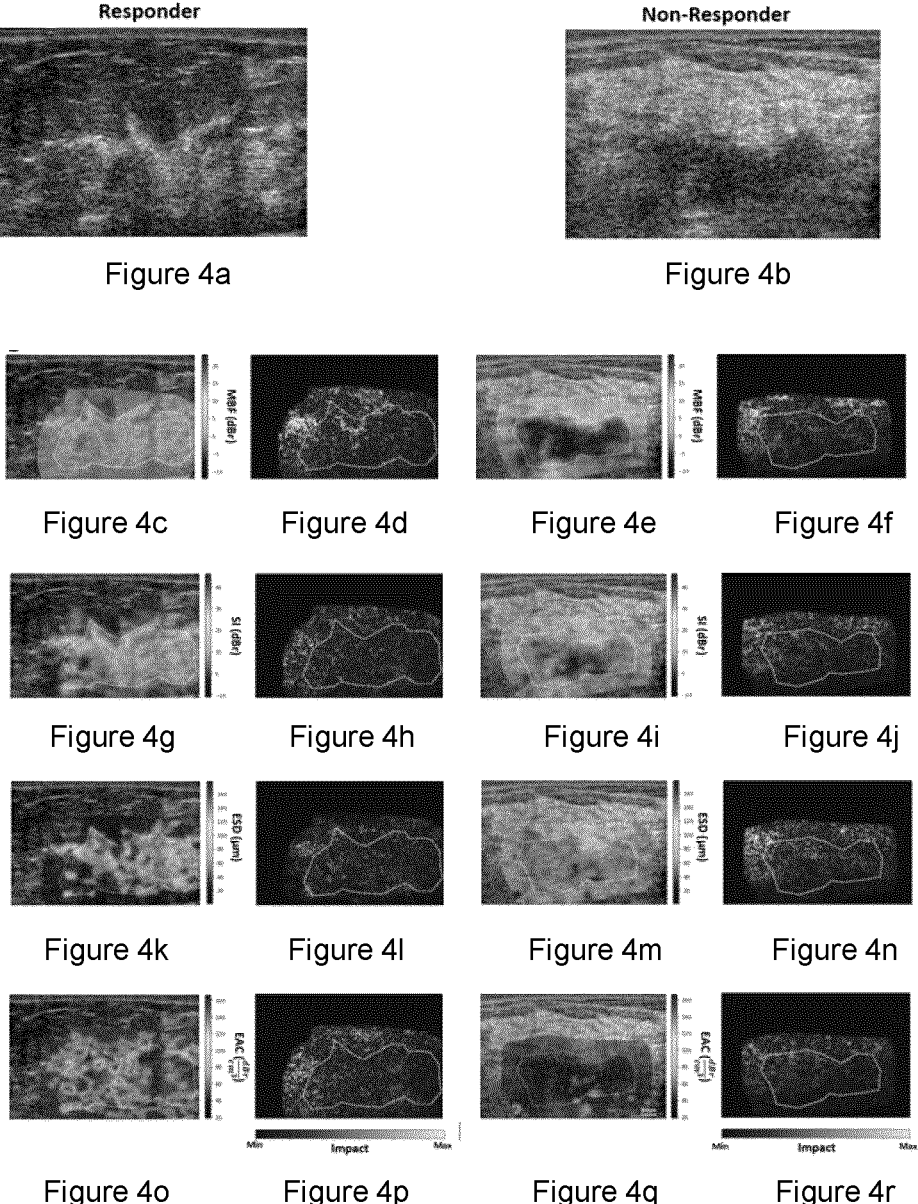
FIGS. 4a and 4b show ultrasound B-mode images.
FIGS. 4c-f show parametric overlays of MBF on B-mode images acquired at pre-treatment from a representative responder and non-responder to NAC, and the associated PDA maps visualizing the level of impact of different regions in each parametric image on the network's decision (model 4 in Table 2), in which the tumor core has been outlined with white dashed line.
FIGS. 4g-j show parametric overlays of SI on B-mode images acquired at pre-treatment from a representative responder and non-responder to NAC, and the associated PDA maps visualizing the level of impact of different regions in each parametric image on the network's decision (model 4 in Table 2), in which the tumor core has been outlined with white dashed line.
FIGS. 4k-n show parametric overlays of ESD on B-mode images acquired at pre-treatment from a representative responder and non-responder to NAC, and the associated PDA maps visualizing the level of impact of different regions in each parametric image on the network's decision (model 4 in Table 2), in which the tumor core has been outlined with white dashed line.
FIGS. 4o-r show parametric overlays of AC on B-mode images acquired at pre-treatment from a representative responder and non-responder to NAC, and the associated PDA maps visualizing the level of impact of different regions in each parametric image on the network's decision (model 4 in Table 2), in which the tumor core has been outlined with white dashed line.
Figure 7A:
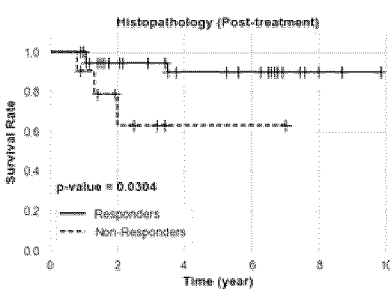
FIG. 7a-e show the ten-year recurrence-free survival curves for the responders and non-responders identified based on the clinical and histological criteria at post treatment, and at pre-treatment using the four predictive models presented in Table 2.
Figure 7B:
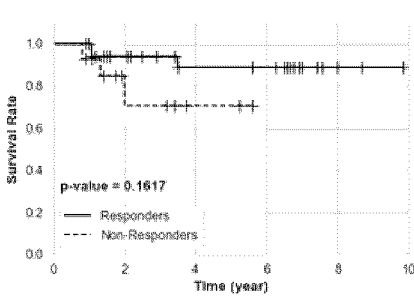
Figure 7C:
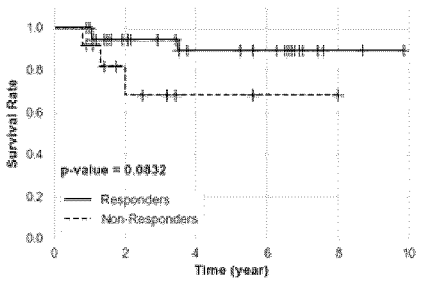
Figure 7D:
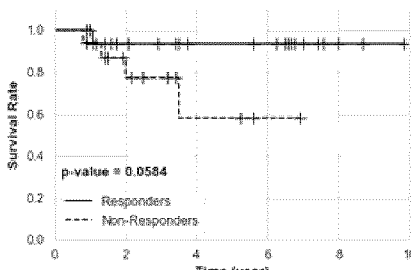
Figure 7E:
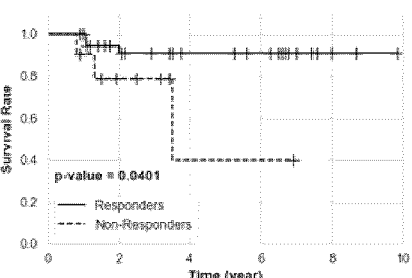

FIGS. 4a-r show QUS parametric maps of MBF, SI, ESD, and EAC overlaid on the ultrasound B-mode images obtained from representative responding and non-responding patients, respectively. As observed in these representative images, the QUS parametric maps associated with the responding and non-responding patients demonstrated different mean and spatial pattern of pixel values within the tumor core and margin. The figures also show the PDA maps associated with these parametric images, visualizing the relative impact of different regions in each image to the network's decision for response prediction. FIGS. 5a and 5b show H&E stained histopathology images of the surgical specimens acquired from representative responding and non-responding patients. In responding patients, minimal tumor cellularity remained within the tumor bed after chemotherapy, as evident in the histopathology slides. In contrast, histopathology images of the non-responding patients typically indicated large areas of residual disease with minimal chemotherapy effects.

Table 2 presents the results of response prediction in different experiments on the validation and independent test sets. The ROC curves associated with the validation and test sets for different predictive models are shown in FIGS. 6a-d. Using the ResNet architecture as the model's backbone to extract feature maps from the parametric images of the tumor core resulted in an AUC of 0.77 on the independent test set. Extending the input parametric images to include both the tumor core and its margin improved the AUC of this model to 0.83.

TABLE 2

Results of response prediction on the validation and independent tests with different predictive models.

| Model | Feature Network | Input Parametric Maps | Validation Set | | | | Test Set | | | |
| | | | Acc | Spec | Sen | Loss | Acc | Spec | Sen | AUC |
| 1 | ResNet | Core | 77% ± 14.8% | 76% | 78% | 0.27 | 80 ± 11.1% | 82.5% | 70% | 0.77 ± 0.12 |
| 2 | ResNet | Core + Margin | 86% ± 12.2% | 90% | 78% | 0.17 | 82 ± 10.6% | 85% | 70% | 0.83 ± 0.10 |
| 3 | RAN | Core | 83% ± 13.2% | 86% | 78% | 0.22 | 80 ± 11.1% | 80% | 80% | 0.82 ± 0.11 |
| 4 | RAN | Core + Margin | 86% ± 12.2% | 90% | 78% | 0.16 | 88 ± 9.0% | 92.5% | 70% | 0.86 ± 0.10 |

Acc: Accuracy ± 95% Confidence Interval; Spec: Specificity; Sen: Sensitivity; AUC: Area under the ROC curve ± 95% Confidence Interval.

Applying the extracted features from the parametric images of the tumor core using the RAN architecture resulted in an accuracy of 80%, and an AUC of 0.82 on the independent test set. Similar to the model with the ResNet architecture as the feature extractor, the overall performance of this model improved by extending the input parametric images to include the tumor margin. In particular, this model resulted in the best prediction performance with an accuracy and AUC of 88%, and 0.86, respectively, on the independent test set. All models demonstrated a relatively similar performance on the validation and test sets, implying a good generalizability of the trained models on never seen samples.

FIG. 7a-e presents the ten-year recurrence-free survival curves for the responders and non-responders identified based on the clinical and histological criteria at post treatment, and at pre-treatment using the four predictive models presented in Table 2. The survival analysis demonstrated a statistically significant difference (p-value=0.030) between the survival curves of the responders and non-responders identified at post-treatment. Among the response cohorts predicted at pre-treatment, the ones identified using the predictive models with the RAN as their feature network demonstrated a statistically significant difference or approached significance. Specifically, whereas the model that input the parametric images of the tumor core approached a significant difference (p-value=0.058), the one with the input parametric images extended to the tumor margin demonstrated a statistically significant difference between the survival of the two predicted cohorts (p-value=0.040). The response cohorts identified by the other two models at pre-treatment did not show a significant difference in survival.

In yet another implementation, a tensor processing unit (TPU) may be employed as an alternative to the GPU 41, which allows for the model to be run in a substantially faster and smoother manner. A TPU is an AI accelerator application-specific integrated circuit (ASIC) specifically for neural network machine learning.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, a GPU, an FPGA, or an ASIC.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system 10 can be interconnected by any form or medium of wireline and/or wireless digital data communication, e.g., a communications network 44. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations, and free-space optical networks. The network may communicate with, for example, Internet Protocol (IP) packets, Frame Relay frames, Asynchronous Transfer Mode (ATM) cells, voice, video, data, and/or other suitable information between network addresses.

The computing system can include clients and servers and/or Internet-of-Things (IoT) devices running publisher/subscriber applications. A client and server are generally remote from each other and typically interact through a communication network. The relationship of client and server arises by virtue of computer programs running on the respective computers and having a client-server relationship to each other.

There may be any number of computers associated with, or external to, the system 10 and communicating over network 44. Further, the terms "client," "user," and other appropriate terminology may be used interchangeably, as appropriate, without departing from the scope of this disclosure.

In another implementation, system 10 follows a cloud computing model, by providing an on-demand network access to a shared pool of configurable computing resources (e.g., servers, storage, applications, and/or services) that can be rapidly provisioned and released with mini-mal or nor resource management effort, including interaction with a service provider, by a user (operator of a thin client).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hard-ware and computer instructions.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises," "comprising," or any other variations thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the steps recited in any of the method or process claims may be executed in any order and are not limited to the order presented. Thus, the preceding detailed description is presented for purposes of illustration only and not of limitation, and the scope of the invention is defined by the preceding description, and with respect to the attached claims.

REFERENCES

[1] H. Sung et al., "Global cancer statistics 2020: GLOBO-CAN estimates of incidence and mortality worldwide for 36 cancers in 185 countries," *CA. Cancer J. Clin.*, February 2021, doi: 10.3322/caac.21660.

[2] F. Bray, J. Ferlay, I. Soerjomataram, R. L. Siegel, L. A. Torre, and A. Jemal, "Global cancer statistics 2018: GLOBOCAN estimates of incidence and mortality worldwide for 36 cancers in 185 countries," *CA. Cancer J. Clin.*, vol. 68, no. 6, pp. 394-424, November 2018, doi: 10.3322/caac.21492.

[3] S. H. Giordano, "Update on Locally Advanced Breast Cancer," *Oncologist, vol.* 8, no. 6, pp. 521-530, December 2003, doi: 10.1634/theoncologist.8-6-521.

[4] G. N. Hortobagyi, "Comprehensive management of locally advanced breast cancer.," *Cancer*, vol. 66, no. 6 Suppl, pp. 1387-91, September 1990, doi: 10.1002/1097-0142(19900915)66:14+<1387::aid-cncr2820661414>3.0.co; 2-i.

[5] G. G et al., "Locally advanced non-metastatic breast cancer: analysis of prognostic factors in 125 patients homogeneously treated with a combined modality approach," *Eur. J. Cancer*, vol. 31A, no. 9, pp. 1428-1433, 1995, doi: 10.1016/0959-8049(95)00199-S.

[6] S. J. Cleator, A. Makris, S. E. Ashley, R. Lal, and T. J. Powles, "Good clinical response of breast cancers to neoadjuvant chemoendocrine therapy is associated with improved overall survival.," *Ann. Oncol. Off. J. Eur. Soc. Med. Oncol.*, vol. 16, no. 2, pp. 267-72, February 2005, doi: 10.1093/annonc/mdi049.

[7] V. Guarneri et al., "Prognostic value of pathologic complete response after primary chemotherapy in relation to hormone receptor status and other factors," *J. Clin. Oncol.*, vol. 24, no. 7, pp. 1037-1044, March 2006, doi: 10.1200/JCO.2005.02.6914.

[8] B. T. Hennessy et al., "Outcome after pathologic complete eradication of cytologically proven breast cancer axillary node metastases following primary chemotherapy," *J. Clin. Oncol.*, vol. 23, no. 36, pp. 9304-9311, 2005, doi: 10.1200/JCO.2005.02.5023.

[9] J. B. Nikas, W. C. Low, and P. A. Burgio, "Prognosis of treatment response (pathological complete response) in breast cancer," *Biomark. Insights*, vol. 7, pp. 59-70, May 2012, doi: 10.4137/BMI.S9387.

[10] B. Fisher et al., "Effect of preoperative chemotherapy on the outcome of women with operable breast cancer," *J. Clin. Oncol.*, vol. 16, no. 8, pp. 2672-2685, 1998, doi: 10.1200/JCO.1998.16.8.2672.

[11] S. H. Giordano, "Update on Locally Advanced Breast Cancer," *Oncologist*, vol. 8, no. 6, pp. 521-530, 2003, doi: 10.1634/theoncologist.8-6-521.

[12] D. Sethi, R. Sen, J. Sen, S. Parshad, S. Khetarpal, and M. Garg, "Histopathologic changes following neoadjuvant chemotherapy in various malignancies," *Int. J. Appl. Basic Med. Res.*, vol. 2, no. 2, p. 111, 2012, doi: 10.4103/2229-516x.106353.

[13] S. Chuthapisith, J. M. Eremin, M. El-Sheemy, and O. Eremin, "Neoadjuvant chemotherapy in women with large and locally advanced breast cancer: Chemoresistance and prediction of response to drug therapy," *Surgeon*, vol. 4, no. 4. Edinburgh University Press, pp. 211-219, 1 Aug. 2006, doi: 10.1016/S1479-666X(06) 80062-4.

[14] W. Haque, V. Verma, S. Hatch, V. Suzanne Klimberg, E. Brian Butler, and B. S. Teh, "Response rates and pathologic complete response by breast cancer molecular subtype following neoadjuvant chemotherapy," *Breast Cancer Res. Treat.*, vol. 170, no. 3, pp. 559-567, August 2018, doi: 10.1007/s10549-018-4801-3.

[15] T. Byrski et al., "Pathologic complete response rates in young women with BRCA1-positive breast cancers after neoadjuvant chemotherapy," *J. Clin. Oncol.*, vol. 28, no. 3, pp. 375-379, January 2010, doi: 10.1200/JCO.2008.20.7019.

[16] K. Brindle, "New approaches for imaging tumour responses to treatment," *Nature Reviews Cancer*, vol. 8, no. 2. pp. 94-107, February 2008, doi: 10.1038/nrc2289.

[17] G. von Minckwitz et al., "S3-2: Neoadjuvant Chemotherapy Adapted by Interim Response Improves Overall Survival of Primary Breast Cancer Patients—Results of the GeparTrio Trial," in *Cancer Research,* 2011, vol. 71, no. 24, doi: 10.1158/0008-5472.sabcs11-s3-2.

[18] G. Von Minckwitz et al., "Neoadjuvant vinorelbine-capecitabine versus docetaxel-doxorubicin-cyclophosphamide in early nonresponsive breast cancer: Phase III randomized gepartrio trial," *J. Natl. Cancer Inst.*, vol. 100, no. 8, pp. 542-551, April 2008, doi: 10.1093/jnci/djn085.

[19] J. Mamou and M. L. Oelze, *Quantitative ultrasound in soft tissues.* Springer Netherlands, 2013.

[20] E. J. Feleppa et al., "Typing of prostate tissue by ultrasonic spectrum analysis," *IEEE Trans. Ultrason. Ferroelectr. Freq. Control*, vol. 43, no. 4, pp. 609-619, July 1996, doi: 10.1109/58.503779.

[21] M. Yang, T. M. Krueger, J. G. Miller, and M. R. Holland, "Characterization of anisotropic myocardial backscatter using spectral slope, intercept and midband fit parameters," *Ultrason. Imaging*, vol. 29, no. 2, pp. 122-134, April 2007, doi: 10.1177/016173460702900204.

[22] D. J. Coleman, F. L. Lizzi, R. H. Silverman, L. Helson, J. H. Torpey, and M. J. Rondeau, "A model for acoustic characterization of intraocular tumors.," *Invest. Ophthalmol. Vis. Sci.*, vol. 26, no. 4, pp. 545-50, April 1985.

[23] H. Tadayyon, A. Sadeghi-Naini, L. Wirtzfeld, F. C. Wright, and G. Czarnota, "Quantitative ultrasound characterization of locally advanced breast cancer by estimation of its scatterer properties," *Med. Phys.*, vol. 41, no. 012903, January 2014, doi: 10.1118/1.4852875.

[24] H. Tadayyon, A. Sadeghi-Naini, and G. J. Czarnota, "Noninvasive characterization of locally advanced breast cancer using textural analysis of quantitative ultrasound parametric images," *Transl. Oncol.*, vol. 7, no. 6, pp. 759-767, 2014, doi: 10.1016/j.tranon.2014.10.007.

[25] A. Sadeghi-Naini et al., "Quantitative ultrasound spectroscopic imaging for characterization of disease extent in prostate cancer patients," *Transl. Oncol.*, vol. 8, no. 1, pp. 25-34, February 2015, doi: 10.1016/j.tranon.2014.11.005.

[26] A. Guimond et al., "Quantitative ultrasonic tissue characterization as a new tool for continuous monitoring of chronic liver remodelling in mice," *Liver Int.*, vol. 27, no. 6, pp. 854-64, August 2007, doi: 10.1111/j.1478-3231.2007.01493.x.

[27] B. Banihashemi, R. Vlad, B. Debeljevic, A. Giles, M. C. Kolios, and G. J. Czarnota, "Ultrasound imaging of apoptosis in tumor response: Novel preclinical monitoring of photodynamic therapy effects," *Cancer Res.*, vol. 68, no. 20, pp. 8590-8596, October 2008, doi: 10.1158/0008-5472.CAN-08-0006.

[28] R. M. Vlad, S. Brand, A. Giles, M. C. Kolios, and G. J. Czarnota, "Quantitative ultrasound characterization of responses to radiotherapy in cancer mouse models," *Clin. Cancer Res.*, vol. 15, no. 6, pp. 2067-2075, March 2009, doi: 10.1158/1078-0432.CCR-08-1970.

[29] G. J. Czarnota et al., "Tumor radiation response enhancement by acoustical stimulation of the vasculature," *Proc. Natl. Acad. Sci. U.S.A.*, vol. 109, no. 30, pp. E2033-E2041, July 2012, doi: 10.1073/pnas.1200053109.

[30] A. Sadeghi-Naini et al., "Low-frequency quantitative ultrasound imaging of cell death in vivo," *Med. Phys.*, vol. 40, no. 8, p. 082901, July 2013, doi: 10.1118/1.4812683.

[31] H. Tadayyon et al., "Quantitative ultrasound assessment of breast tumor response to chemotherapy using a multi-parameter approach," *Oncotarget*, vol. 7, no. 29, pp. 45094-45111, July 2016, doi: 10.18632/oncotarget.8862.

[32] L. Sannachi et al., "Non-invasive evaluation of breast cancer response to chemotherapy using quantitative ultrasonic backscatter parameters," *Med. Image Anal.*, vol. 20, no. 1, pp. 224-236, February 2015, doi: 10.1016/j.media.2014.11.009.

[33] A. Sadeghi-Naini et al., "Quantitative ultrasound evaluation of tumor cell death response in locally advanced breast cancer patients receiving chemotherapy," *Clin. Cancer Res.*, vol. 19, no. 8, pp. 2163-2173, April 2013, doi: 10.1158/1078-0432.CCR-12-2965.

[34] D. DiCenzo et al., "Quantitative ultrasound radiomics in predicting response to neoadjuvant chemotherapy in patients with locally advanced breast cancer: Results from multi-institutional study," *Cancer Med.*, vol. 9, no. 16, pp. 5798-5806, August 2020, doi: 10.1002/cam4.3255.

[35] A. Sadeghi-Naini et al., "Conventional frequency ultrasonic biomarkers of cancer treatment response in vivo," *Transl. Oncol.*, vol. 6, no. 3, pp. 234-243, 2013, doi: 10.1593/tlo.12385.

[36] A. Sadeghi-Naini et al., "Chemotherapy-Response Monitoring of Breast Cancer Patients Using Quantitative Ultrasound-Based Intra-Tumour Heterogeneities," *Sci. Rep.*, vol. 7, no. 10352, December 2017, doi: 10.1038/s41598-017-09678-0.

[37] A. Sadeghi-Naini et al., "Early prediction of therapy responses and outcomes in breast cancer patients using quantitative ultrasound spectral texture," *Oncotarget*, vol. 5, no. 11, pp. 3497-3511, 2014, doi: 10.18632/oncotarget.1950.

[38] A. Dasgupta et al., "Quantitative ultrasound radiomics using texture derivatives in prediction of treatment response to neo-adjuvant chemotherapy for locally advanced breast cancer," *Oncotarget*, vol. 11, no. 42, pp. 3782-3792, October 2020, doi: 10.18632/oncotarget.27742.

[39] H. Tadayyon et al., "A priori Prediction of Neoadjuvant Chemotherapy Response and Survival in Breast Cancer Patients using Quantitative Ultrasound," *Sci. Rep.*, vol. 7, no. 45733 (2017), April 2017, doi: 10.1038/srep45733.

[40] D. Shen, G. Wu, and H.-I. Suk, *Deep Learning in Medical Image Analysis*. Elsevier, 2017.

[41] G. Litjens et al., "A survey on deep learning in medical image analysis," *Medical Image Analysis*, vol. 42. pp. 60-88, 1 Dec. 2017, doi: 10.1016/j.media.2017.07.005.

[42] I. Goodfellow, Y. Bengio, A. Courville, and Y. Bengio, "Deep learning," 2016, doi: 10.4258/hir.2016.22.4.351.

[43] K. Ravichandran, N. Braman, A. Janowczyk, and A. Madabhushi, "A deep learning classifier for prediction of pathological complete response to neoadjuvant chemotherapy from baseline breast DCE-MRI," in *Medical Imaging* 2018: *Computer-Aided Diagnosis,* 2018, vol. 10575, p. 11, doi: 10.1117/12.2294056.

[44] Y. Qu, H. Zhu, K. Cao, X. Li, M. Ye, and Y. Sun, "Prediction of pathological complete response to neoadjuvant chemotherapy in breast cancer using a deep learning (DL) method," *Thorac. Cancer,* vol. 11, no. 3, pp. 651-658, March 2020, doi: 10.1111/1759-7714.13309.

[45] R. Ha et al., "Prior to Initiation of Chemotherapy, Can We Predict Breast Tumor Response? Deep Learning Convolutional Neural Networks Approach Using a Breast MRI Tumor Dataset," *J. Digit. Imaging,* vol. 32, no. 5, pp. 693-701, October 2019, doi: 10.1007/s10278-018-0144-1.

[46] M. Byra, H. Piotrzkowska-Wroblewska, K. Dobruch-Sobczak, and A. Nowicki, "Combining Nakagami imaging and convolutional neural network for breast lesion classification," in *IEEE International Ultrasonics Symposium, IUS,* 2017, pp. 1-4, doi: 10.1109/ULTSYM.2017.8092154.

[47] F. Wang et al., "Residual Attention Network for Image Classification," *Proc.—30th IEEE Conf. Comput. Vis. Pattern Recognition, CVPR* 2017, vol. 2017—January, pp. 6450-6458, April 2017.

[48] K. He, X. Zhang, S. Ren, and J. Sun, "Deep residual learning for image recognition," in *Proceedings of the IEEE Computer Society Conference on Computer Vision and Pattern Recognition,* 2016, vol. 2016—December, pp. 770-778, doi: 10.1109/CVPR.2016.90.

[49] E. A. A. Eisenhauer et al., "New response evaluation criteria in solid tumours: Revised RECIST guideline (version 1.1)," *Eur J Cancer,* no. 14865, pp. 228-247, January 2009, doi: 10.1016/j.ejca.2008.10.026.

[50] K. N. Ogston et al., "A new histological grading system to assess response of breast cancers to primary chemotherapy: prognostic significance and survival," *The Breast,* vol. 12, no. 5, pp. 320-327, October 2003, doi: 10.1016/S0960-9776(03)00106-1.

[51] H. Taleghamar, H. Moghadas-Dastjerdi, G. J. Czarnota, and A. Sadeghi-Naini, "Characterizing intra-tumor regions on quantitative ultrasound parametric images to predict breast cancer response to chemotherapy at pre-treatment," *Sci. Rep.,* vol. 11, no. 14865, July 2021, doi: 10.1038/s41598-021-94004-y.

[52] Y. Labyed, T. A. Bigelow, and B. L. McFarlin, "Estimate of the attenuation coefficient using a clinical array transducer for the detection of cervical ripening in human pregnancy," *Ultrasonics,* vol. 51, no. 1, pp. 34-39, January 2011, doi: 10.1016/j.ultras.2010.05.005.

[53] L. X. Yao, J. A. Zagzebski, and E. L. Madsen, "Backscatter coefficient measurements using a reference phantom to extract depth-dependent instrumentation factors," *Ultrason. Imaging,* vol. 12, no. 1, pp. 58-70, January 1990, doi: 10.1016/0161-7346(90)90221-i.

[54] F. L. Lizzi et al., "Comparison of theoretical scattering results and ultrasonic data from clinical liver examinations," *Ultrasound Med. Biol.,* vol. 14, no. 5, pp. 377-385, 1988.

[55] M. F. Insana, R. F. Wagner, D. G. Brown, and T. J. Hall, "Describing small-scale structure in random media using pulse-echo ultrasound," *J. Acoust. Soc. Am.,* vol. 87, no. 1, pp. 179-92, January 1990.

[56] M. L. Oelze, W. D. O'Brien, J. P. Blue, and J. F. Zachary, "Differentiation and characterization of rat mammary fibroadenomas and 4T1 mouse carcinomas using quantitative ultrasound imaging," *IEEE Trans. Med. Imaging,* vol. 23, no. 6, pp. 764-771, June 2004, doi: 10.1109/TMI.2004.826953.

[57] M. F. Insana and T. J. Hall, "Parametric ultrasound imaging from backscatter coefficient measurements: image formation and interpretation," *Ultrason. Imaging,* vol. 12, no. 4, pp. 245-67, October 1990.

[58] A. Sadeghi-Naini et al., "Breast-Lesion Characterization using Textural Features of Quantitative Ultrasound Parametric Maps," *Sci. Rep.,* vol. 7, no. 13638, December 2017, doi: 10.1038/S41598-017-13977-X.

[59] K. A. Topp, J. F. Zachary, and J. O'Brien, "Quantifying B-mode images of in vivo rat mammary tumors by the frequency dependence of backscatter," *J. Ultrasound Med.,* vol. 20, no. 6, pp. 605-612, 2001, doi: 10.7863/JUM.2001.20.6.605.

[60] D. P. Kingma and J. L. Ba, "Adam: A method for stochastic optimization," in *3rd International Conference on Learning Representations, ICLR* 2015—*Conference Track Proceedings,* 2015.

[61] L. M. Zintgraf, T. S. Cohen, T. Adel, and M. Welling, "Visualizing Deep Neural Network Decisions: Prediction Difference Analysis," *5th Int. Conf. Learn. Represent. ICLR* 2017—*Conf. Track Proc.,* February 2017.

[62] L. Sannachi et al., "Response monitoring of breast cancer patients receiving neoadjuvant chemotherapy using quantitative ultrasound, texture, and molecular features," *PLoS One,* vol. 13, no. 1, p. e0189634, January 2018, doi: 10.1371/journal.pone.0189634.

[63] M. Byra, A. Nowicki, H. Wróblewska-Piotrzkowska, and K. Dobruch-Sobczak, "Classification of breast lesions using segmented quantitative ultrasound maps of homodyned K distribution parameters," *Med. Phys.,* vol. 43, no. 10, pp. 5561-5569, October 2016, doi: 10.1118/1.4962928.

[64] J. Wu, G. Gong, Y. Cui, and R. Li, "Intratumor partitioning and texture analysis of dynamic contrast-enhanced (DCE)-MRI identifies relevant tumor subregions to predict pathological response of breast cancer to neoadjuvant chemotherapy," *J. Magn. Reson. Imaging,* vol. 44, no. 5, pp. 1107-1115, November 2016, doi: 10.1002/jmri.25279.

[65] A. Sadeghi-Naini et al., "Early detection of chemotherapy-refractory patients by monitoring textural alterations in diffuse optical spectroscopic images," *Med. Phys.,* vol. 42, no. 11, pp. 6130-6146, November 2015, doi: 10.1118/1.4931603.

[66] E. Karami et al., "Quantitative MRI Biomarkers of Stereotactic Radiotherapy Outcome in Brain Metastasis," *Sci. Rep.,* vol. 9, no. 19830, December 2019, doi: 10.1038/s41598-019-56185-5.

[67] P. M. Lamb, N. M. Perry, S. J. Vinnicombe, and C. A. Wells, "Correlation between ultrasound characteristics, mammographic findings and histological grade in patients with invasive ductal carcinoma of the breast," *Clin. Radiol.,* vol. 55, no. 1, pp. 40-44, 2000, doi: 10.1053/crad.1999.0333.

[68] A. M. Fowler, D. A. Mankoff, and B. N. Joe, "Imaging Neoadjuvant Therapy Response in Breast Cancer," *Radiology,* vol. 285, no. 2, pp. 358-375, November 2017, doi: 10.1148/radiol.2017170180.

The invention claimed is:

1. A system for predicting breast cancer response to neo-adjuvant chemotherapy (NAC) using quantitative ultrasound (QUS) parametric images and/or B-mode images, the system comprising:

an imaging system for acquiring at least one ultrasound data frame comprising a raw RF signal, and/or an image;

a computer system comprising a hardware processor and a memory device on which instructions are encoded to cause the hardware processor to perform the operations of:

receiving the at least one ultrasound data frame and using one or more predefined rules to identify a region of interest (ROI) in each of the at least one ultrasound data frame, the ROI comprising a tumor, and the ROI may be identified automatically;

generating, from the at least one ultrasound data frame at least one quantitative ultrasound (QUS) parametric map and/or processed B-mode image for the tumor;

with a feature network of a machine learning architecture, extracting optimal feature maps from the QUS parametric images and/or B-mode images;

inputting the optimal feature maps into a prediction network of the machine learning architecture, the optimized feature maps obtained from the feature network are combined or averaged over all images associated with each tumor, the feature and prediction networks may be integrated in an end-to-end system, preprocessing the QUS parametric images and/or B-mode images and formatting them to generate a training dataset for a deep learning model, training the feature network to generate the optimal feature maps for single QUS parametric images and/or B-mode images;

training the predictive network by using a combination of, or averaged, feature vectors associated with each patient in the training dataset, in case of an end-to-end system mentioned above, the integrated feature and prediction networks are trained together; and classifying the tumor subject into a responder or a non-responder to the NAC, and classifying a response to as at least one of a complete response, partial response, stable disease, or progressive disease.

2. The system of claim 1, wherein the at least one ultrasound data frame comprises at least one of an ultrasound B-mode image and radiofrequency (RF) data.

3. The system of claim 1, wherein the parametric maps are generated for all imaging planes of the tumor using a sliding window analysis throughout the region of interest.

4. The system of claim 3, wherein the sliding window size is selected such that the sliding window covers sufficient ultrasound wavelengths in an axial direction for spectral analysis while preserving texture in generated parametric maps, with an overlap size to obtain isotropic pixels.

5. The system of claim 1, wherein the machine learning architecture comprises at least one of a deep convolutional neural network (DCNN) architecture, a deep learning architecture, and a transformer architecture.

6. The system of claim 5, wherein the deep convolutional neural network (DCNN) architecture comprises a residual network (ResNet) architecture.

7. The system of claim 5, wherein the deep convolutional neural network (DCNN) architecture comprises a residual attention network (RAN) architecture.

8. The system of claim 1, wherein the imaging system is an ultrasound imaging system.

9. The system of claim 8, wherein the optimized feature maps obtained from the feature network are averaged over all parametric images associated with each tumor.

10. The system of claim 9, wherein the averaged optimized feature maps are subsequently input into the predictive network adapted for response prediction at the patient level.

11. The system of claim 10, wherein the predictive network comprises fully-connected layers with an input layer, a middle layer, and a softmax layer at the end with an output size of two to predict the probability of the response categories (responder versus non-responder) for each patient.

12. The system of claim 11, wherein the input layer comprises the same size as a flatten feature vector (256) and the middle layer comprises 100 neurons.

13. The system of claim 12, wherein drop-out layers are added after each layer to minimize overfitting and enhance its generalization performance.

14. The system of claim 1, wherein the parametric images of the training set are preprocessed by resampling parametric images to a predefined pixel size, wherein the pixel values in the parametric images of the training set are normalized to (0 1) to facilitate the training convergence.

15. The system of claim 14, wherein training set normalization parameters are used for normalization and data augmentation is applied on the training dataset.

16. The system of claim 15, wherein the training dataset is augmented by at least flipping the parametric images horizontally and shifting both horizontally and vertically.

17. The system of claim 15, wherein the feature network is trained to generate the optimal feature maps for single QUS parametric images by inputting the parametric images into the feature network.

18. The system of claim 17, wherein the optimal feature maps are acquired for each imaging plane by feeding its corresponding parametric images into the trained feature network.

19. The system of claim 18, wherein the optimal features are calculated for all 2D imaging planes of the tumor, flattened to a 1D vector, and subsequently averaged over the entire tumor volume to obtain an averaged feature vector used in the predictive network.

20. The system of claim 19, wherein the predictive network is trained using the averaged feature vectors associated with the patients in the training dataset, and evaluated over the independent test set for response prediction.

21. A method for predicting a response to neo-adjuvant chemotherapy (NAC) using quantitative ultrasound (QUS) parametric images, the method comprising:

with an imaging system, acquiring at least one ultrasound data frame comprising a raw RF signal, and/or an image;

with a computer system comprising a hardware processor and a memory device on which instructions are encoded to cause the hardware processor performing the operations of:

receiving the at least one ultrasound data frame and using one or more predefined rules to identify a region of interest (ROI) in each of the at least one ultrasound data frame, the ROI comprising a tumor, and the ROI may be identified automatically;

generating, from the at least one ultrasound data frame at least one quantitative ultrasound (QUS) parametric map and/or processed B-mode image for the tumor;

with a feature network of a machine learning architecture, extracting optimal feature maps from the QUS parametric images and/or B-mode images;

inputting the optimal feature maps into a prediction network of the machine learning architecture, the optimized feature maps obtained from the feature network are combined or averaged over all images associated with each tumor, the feature and prediction networks may be integrated in an end-to-end system, preprocessing the QUS parametric images and/or B-mode images and formatting them to generate a training dataset for a deep learning model, training the feature network to generate the optimal feature maps for single QUS parametric images and/or B-mode images;

training the predictive network by using a combination of, or averaged, feature vectors associated with each patient in the training dataset, in case of an end-to-end system mentioned above, the integrated feature and prediction networks are trained together; and classifying the tumor subject into a responder or a non-responder to the NAC, and classifying a response to as at least one of a complete response, partial response, stable disease, or progressive disease.

* * * * *